United States Patent
Souza et al.

(10) Patent No.: US 10,407,396 B2
(45) Date of Patent: Sep. 10, 2019

(54) CRYSTALLINE FORM OF SELEXIPAG

(71) Applicant: Apotex Inc., Toronto (CA)

(72) Inventors: Fabio E. S. Souza, Mississauga (CA); Bahareh Khalili, Mississauga (CA); Katherine A. Rantanen, Burlington (CA); Annyt Bhattacharyya, Hamilton (CA); Jenny L. Gerster, Brantford (CA); Allan W. Rey, Brantford (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/185,223

(22) Filed: Nov. 9, 2018

(65) Prior Publication Data

US 2019/0144397 A1 May 16, 2019

Related U.S. Application Data (60) Provisional application No. 62/587,099, filed on Nov. 16, 2017.

(51) Int. Cl.
*C07D 241/20* (2006.01)
*A61K 9/20* (2006.01)

(52) U.S. Cl.
CPC .............. *C07D 241/20* (2013.01); *A61K 9/20* (2013.01); *C07B 2200/13* (2013.01)

(58) Field of Classification Search
CPC .................................................. C07D 241/20
See application file for complete search history.

(56) References Cited

U.S. PATENT DOCUMENTS

| | | | | |
|---|---|---|---|---|
| 7,205,302 | B2 * | 4/2007 | Asaki ................. | A61K 31/4418 514/241 |
| 8,629,145 | B2 * | 1/2014 | Kuwano ............. | C07D 241/20 514/217.05 |
| 8,791,122 | B2 | 7/2014 | Itou | |
| 8,889,693 | B2 * | 11/2014 | Murakami .......... | C07D 241/20 514/255.06 |
| 10,040,771 | B2 * | 8/2018 | Tang ................... | C07D 241/20 |
| 10,188,648 | B2 * | 1/2019 | Villalva .............. | C07D 241/20 |
| 2018/0029998 | A1 * | 2/2018 | Tang ................... | C07D 241/20 |
| 2018/0214446 | A1 * | 8/2018 | Villalva .............. | C07D 241/20 |
| 2018/0221447 | A1 * | 8/2018 | Kumar ................ | A61K 38/179 |
| 2019/0112277 | A1 * | 4/2019 | Parthasaradhi Reddy ................. A61K 31/4965 |

FOREIGN PATENT DOCUMENTS

| WO | 2017040872 A1 | 3/2017 |
|---|---|---|
| WO | 2017121806 A1 | 7/2017 |
| WO | 2018008042 A1 | 1/2018 |
| WO | 2018015974 A1 | 1/2018 |
| WO | 2018022704 A1 | 2/2018 |

OTHER PUBLICATIONS

K. Morrison et al., The Journal of Pharmacology and Experimental Therapeutics, 249-255 (2010) (Year: 2010).*
A.J. Cruz-Cabeza et al., 44 Chemical Society Reviews, 8619-8635 (2015) (Year: 2015).*
Solid State Characterization of Pharmaceuticals 473-491, 490 (R.A. Storey et al., eds., 2011) (Year: 2011).*
Bernstein, "Is this Material Polymorphic?", Polymorphism in Molecular Crystals, 2002, pp. 9-10, Oxford University Press, New York.
Porter, "Coating of Pharmaceutical Dosage Forms", Remington The Science and Practice of Pharmacy, 2006, pp. 929-938, Lippincott Williams & Wilkins, Philadelphia.
Rudnic et al., "Oral Solid Dosage Forms", Remington the Science and Practice of Pharmacy, 2006, pp. 889-928, Lippincott Williams & Wilkins, Philadelphia.
"Australian Public Assessment Report for Selexipag", Therapeutic Goods Administration, 2016. 90 Pages.

* cited by examiner

*Primary Examiner* — Alexander R Pagano
(74) *Attorney, Agent, or Firm* — The Webb Law Firm (57) ABSTRACT

The present invention provides a novel crystalline form of Selexipag, Selexipag Form APO-I, which is a methanol solvate of Selexipag, compositions thereof, and the use of this crystalline form in the treatment of pulmonary arterial hypertension.

19 Claims, 3 Drawing Sheets

CRYSTALLINE FORM OF SELEXIPAG

CROSS-REFERENCE TO RELATED APPLICATION

This application claims the benefit of U.S. Provisional Patent Application No. 62/587,099, filed Nov. 16, 2017, the disclosure of which is hereby incorporated in its entirety by reference.

TECHNICAL FIELD

The present invention is directed to a novel crystalline form of Selexipag and processes for the preparation thereof.

BACKGROUND

The compound 2-{4-[N-(5,6-diphenylpyrazin-2-yl)-N-isopropylamino]butyloxy}-N-(methylsulfonyl)acetamide, commonly known as Selexipag, is described in U.S. Pat. No. 7,205,302 B2. Selexipag is a prostacyclin PGI2 receptor agonist, marketed in the United States as UPTRAVI®, and is indicated for the treatment of pulmonary arterial hypertension (PAH, WHO Group 1) to delay disease progression and reduce the risk of hospitalization for PAH.

(1)

Crystalline forms of Selexipag are known, and have been disclosed, for example, in U.S. Pat. No. 8,791,122 B2, which reports non-solvated Selexipag Forms I, II and III, and WO 2017/040872 A1, which reports Forms IV and V. WO 2017/121806 A1 discloses equimolar solvates of Selexipag with aromatic hydrocarbons including o-xylene, chlorobenzene and toluene, which are reported to be useful in the provision of amorphous solid dispersions of Selexipag with a pharmaceutically acceptable excipient.

According to publicly available regulatory approval documents for Selexipag, such as the Australian Public Assessment Report (AusPAR), the drug substance Selexipag in the approved drug product UPTRAVI®, is Form I. This form of the drug substance is reported to exhibit pH dependent solubility and to fall within Class II of the Biopharmaceutics Classification System (BCS). Class II drug substances have high permeability but low solubility, which can present a challenge to achieving good bioavailability. Approaches to improving solubility and bioavailability of a particular crystalline form of a Class II drug substance include, for example, particle size reduction techniques, dispersion of the drug substance onto an inert carrier, and formulation together with solubilizing excipients. According to AusPAR, the drug substance Selexipag in the approved drug product UPTRAVI®, is subjected to micronisation to facilitate dissolution in the drug product.

A further consideration in the provision of a formulated Selexipag drug product is associated with the high potency of the drug substance given that the dose of Selexipag in the marketed UPTRAVI® tablets ranges from 200 μg to 1.6 mg. There are many challenges in manufacturing high potency drug substances that are related to, for example, safe handling practices to avoid inadvertent exposures, achieving content uniformity or homogeneity within the formulated product, accurate determination of the drug content in unit doses and effectively demonstrating cleanliness of equipment at very low detection levels.

Because Selexipag possesses the challenging characteristics of both low solubility and high potency, both particle size distribution (PSD) and polymorphism are two critical quality attributes (CQAs) that need to be strictly monitored and controlled in order to ensure consistent drug product performance (i.e., dissolution rate, bioavailability, solubility, stability, appearance, absorption and uniformity of content in low-dose tablets) and manufacturability of a solid dosage form (i.e., granulation, milling, flow properties of the blend for compression and encapsulation).

Different crystalline forms of the same compound may have different packing, thermodynamic, spectroscopic, kinetic, surface and mechanical properties. For example, different crystalline forms may have different stability properties such that a particular crystalline form may be less sensitive to heat, relative humidity (RH) and/or light. Alternatively or additionally, a particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form. Particular crystalline forms may also have different solubilities, thereby providing different pharmacokinetic parameters, which allow for specific crystalline forms to be used in order to achieve specific pharmacokinetic targets. Differences in solubility between crystalline forms are particularly relevant for drug substances exhibiting low aqueous solubility, such that even a modest increase in solubility may provide a beneficial enhancement in bioavailability.

Additionally, the particle size of a given crystalline form upon isolation from a suitable crystallisation system may be finer than a different crystalline form, corresponding with increased surface area and the potential for enhanced solubility. Particle size can be particularly critical for high potency substances, and smaller particles are generally preferred during the formulation of high potency drug substances to ensure content uniformity in the dosage form. Different physical properties of crystalline forms may also affect their processing. For example, the particle morphology or crystal habit of a particular crystalline form may result in differences in bulk properties such as flow rates and density, resulting in more resistance to flow, or inefficiency during filtration and/or washing. Furthermore, particle morphology can have an impact on micronisation practices that are typically used to further reduce the particle size of high potency drugs, with some morphologies being more resistant to breakage and processing than others.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Particularly due to the low solubility and high potency characteristics of Selexipag, both of which lead to considerations related to crystalline form, there exists a need for novel crystalline forms of Selexipag for use in providing improved drug products containing Selexipag and their manufacture.

SUMMARY

The Selexipag crystalline form of the present invention exhibits differences in properties when compared to the known crystalline forms of Selexipag. Properties that differ between the invention and known crystalline forms of Selexipag include packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tableting, handling, flow, and blending.

Differences in the properties of the crystalline form of the present invention provide practical advantages that can be exploited to meet specific needs in the manufacture and formulation of Selexipag. For example, solvated crystalline forms of Selexipag are reported to be useful as intermediates in the production of solid amorphous dispersions thereof, which may be preferred when developing Selexipag due to the opportunity for both solubility enhancement and improvement of content uniformity associated with amorphous dispersions. However, procedures available for the preparation of known solvated crystalline forms of Selexipag require lengthy stirring periods at sub-zero temperatures. Furthermore, the known solvated forms of Selexipag incorporate equimolar amounts of high molecular weight aromatic hydrocarbon solvents, which translates into Selexipag having 15-18 weight percentage of solvent.

The present invention provides a crystalline solvated form of Selexipag that can be prepared by an efficient and industrially compatible process at temperatures above freezing using the universal solvent methanol, which has lower toxicity than the aromatic hydrocarbon solvents used to prepare the known solvated forms of Selexipag (xylenes, toluene and chlorobenzene). In addition, the Selexipag crystalline form of the present invention incorporates half the molar amount, and a fifth the weight percentage, of solvent compared to the known solvated forms.

The formation of the crystalline solvate form of the present invention is particularly unexpected in light of the previous disclosure in U.S. Pat. No. 8,791,122 B2 that methanol as a crystallization solvent yields mixtures of Form II and Form III, and not the solvated form of the present invention as disclosed herein.

Accordingly, in a first aspect of the present invention, there is provided a methanol solvate of Selexipag. Preferably, in the methanol solvate of the first aspect, the molar ratio of Selexipag to methanol is between approximately 1:0.25 and 1:0.75. More preferably, the molar ratio of Selexipag to methanol is approximately 1:0.5.

In a second aspect of the present invention, there is provided a methanol solvate of Selexipag, Form APO-I, characterized by a PXRD diffractogram comprising peaks, expressed in degrees 2θ (±0.2°), at 7.5°, 12.4° and 21.7°. In a preferred embodiment of the second aspect, the PXRD diffractogram further comprises at least three peaks, expressed in degrees 2θ (±0.2°), selected from the group consisting of: 9.4°, 11.6°, 14.1°, 15.1°, 16.7°, 17.2°, 18.3°, 19.9°, 22.3° and 23.6°. In a further preferred embodiment of the second aspect, the PXRD diffractogram further comprises peaks, expressed in degrees 2θ (±0.2°), at 9.4°, 11.6°, 14.1°, 15.1°, 16.7°, 17.2°, 18.3°, 19.9°, 22.3° and 23.6°. More preferably, the Form APO-I methanol solvate provides a PXRD diffractogram comprising peaks in substantially the same positions (±0.2° 2θ) as those shown in FIG. 1. In another preferred embodiment of the second aspect, the Form APO-I methanol solvate is characterized by a DSC thermogram comprising an endothermic peak with a peak onset at approximately 55° C. and a peak maximum at approximately 73° C. More preferably, the DSC thermogram is substantially the same as the representative DSC thermogram provided in FIG. 2. In this second aspect of the invention, the molar ratio of Selexipag to methanol is preferably approximately 1:0.5.

In a third aspect of the present invention, there is provided a process for the preparation of a methanol solvate of Selexipag according to the first or second aspects of the invention, the process comprising:
(1) Dissolving Selexipag in methanol at a suitable temperature to provide a solution;
(2) Seeding the solution with:
　(a) first seeds comprising the methanol solvate of the first or second aspects of the invention;
　(b) second seeds comprising the crystalline form of the sixth aspect of the invention; or
　(c) a combination of the first and second seeds;
　to provide a mixture;
(3) Cooling the mixture, if necessary, to form a suspension; and
(4) Filtering the suspension to isolate a methanol solvate of Selexipag.

In a preferred embodiment of the third aspect, the solution is seeded with the first seeds. In another preferred embodiment of the third aspect, the solution is seeded with the second seeds. In another preferred embodiment of the third aspect of the invention, the suitable temperature is between approximately 50° C. and approximately 70° C. In another preferred embodiment of the third aspect of the invention, the mixture is cooled to a temperature of between approximately 0° C. and approximately 5° C. In another preferred embodiment of the third aspect, the molar ratio of Selexipag to methanol in the methanol solvate is between approximately 1:0.25 and approximately 1:0.75. Most preferably, the molar ratio of Selexipag to methanol in the methanol solvate is approximately 1:0.5. In preferred embodiments of the third aspect of the invention, the methanol solvate prepared is preferably a methanol solvate according to the second aspect of the invention.

In a fourth aspect of the present invention, there is provided a pharmaceutical composition comprising a methanol solvate of Selexipag according to the first or second aspects of the invention, and one or more pharmaceutically acceptable excipients. Preferably, the pharmaceutical composition is in the form of a solid dosage form. More preferably, the pharmaceutical composition is a tablet. Most preferably, the pharmaceutical composition comprises an amount of the methanol solvate equivalent to 0.2 mg, 0.4 mg, 0.6 mg, 0.8 mg, 1 mg, 1.2 mg, 1.4 mg or 1.6 mg Selexipag.

In a fifth aspect of the present invention, there is provided a use of a methanol solvate of Selexipag according to the first or second aspects of the invention in the treatment of pulmonary arterial hypertension.

In a sixth aspect of the present invention, there is provided seed crystals of Selexipag prepared by crystallization of Selexipag from diethylene glycol that are used in the preparation of Selexipag Form APO-I. In a preferred embodiment of the sixth aspect, this crystalline material is characterized by a PXRD diffractogram comprising peaks, expressed in degrees 2θ (±0.2°), at 9.0°, 9.4° and 13.5°. More preferably, the PXRD diffractogram further comprises at least three peaks, expressed in degrees 2θ (±0.2°), selected from the group consisting of: 9.8°, 12.9°, 14.1°, 16.6°, 17.2°, 18.9°, 19.4°, 20.7° and 22.6°. Even more preferably, the PXRD diffractogram further comprises peaks, expressed in degrees 2θ (±0.2°), at 9.8°, 12.9°, 14.1°, 16.6°, 17.2°, 18.9°, 19.4°, 20.7° and 22.6°. Most preferably, the crystalline form provides a PXRD diffractogram comprising peaks in substantially the same positions (±0.2° 2θ) as those shown in FIG. 3.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The Selexipag crystalline form of the present invention exhibits differences in properties when compared to the known crystalline forms of Selexipag. Properties that differ between the invention and known crystalline forms of Selexipag include packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactability, tableting, handling, flow, and blending.

Differences in the properties of the crystalline form of the present invention provide practical advantages that can be exploited to meet specific needs in the manufacture and formulation of Selexipag. For example, solvated crystalline forms of Selexipag are reported to be useful as intermediates in the production of solid amorphous dispersions thereof, which may be preferred when developing a product like Selexipag due to the opportunity for both solubility enhancement and improvement of content uniformity associated with amorphous dispersions. However, procedures available for preparation of known solvated crystalline forms of Selexipag require lengthy stirring periods at sub-zero temperatures. Furthermore, the known solvated forms of Selexipag incorporate equimolar amounts of high molecular weight aromatic hydrocarbon solvents, which translates into Selexipag having 15-18 weight percentage of solvent.

The present invention provides a crystalline solvated form that can be prepared by an efficient and industrially compatible process at temperatures above freezing using the universal solvent methanol, which has lower toxicity than the aromatic hydrocarbon solvents used to prepare the known solvated forms of Selexipag (xylenes, toluene and chlorobenzene). In addition, the Selexipag crystalline form of the present invention incorporates half the molar amount, and a fifth the weight percentage, of solvent compared to the known solvated forms.

It is not currently possible to predict what, if any, crystalline forms of a substance exist and furthermore what their properties will be. The formation of the crystalline solvate form of the present invention is particularly unexpected in light of the previous disclosure in U.S. Pat. No. 8,791,122 B2 that methanol as a crystallization solvent yields mixtures of Form II and Form III and not a solvate form as disclosed herein.

Figure 1:
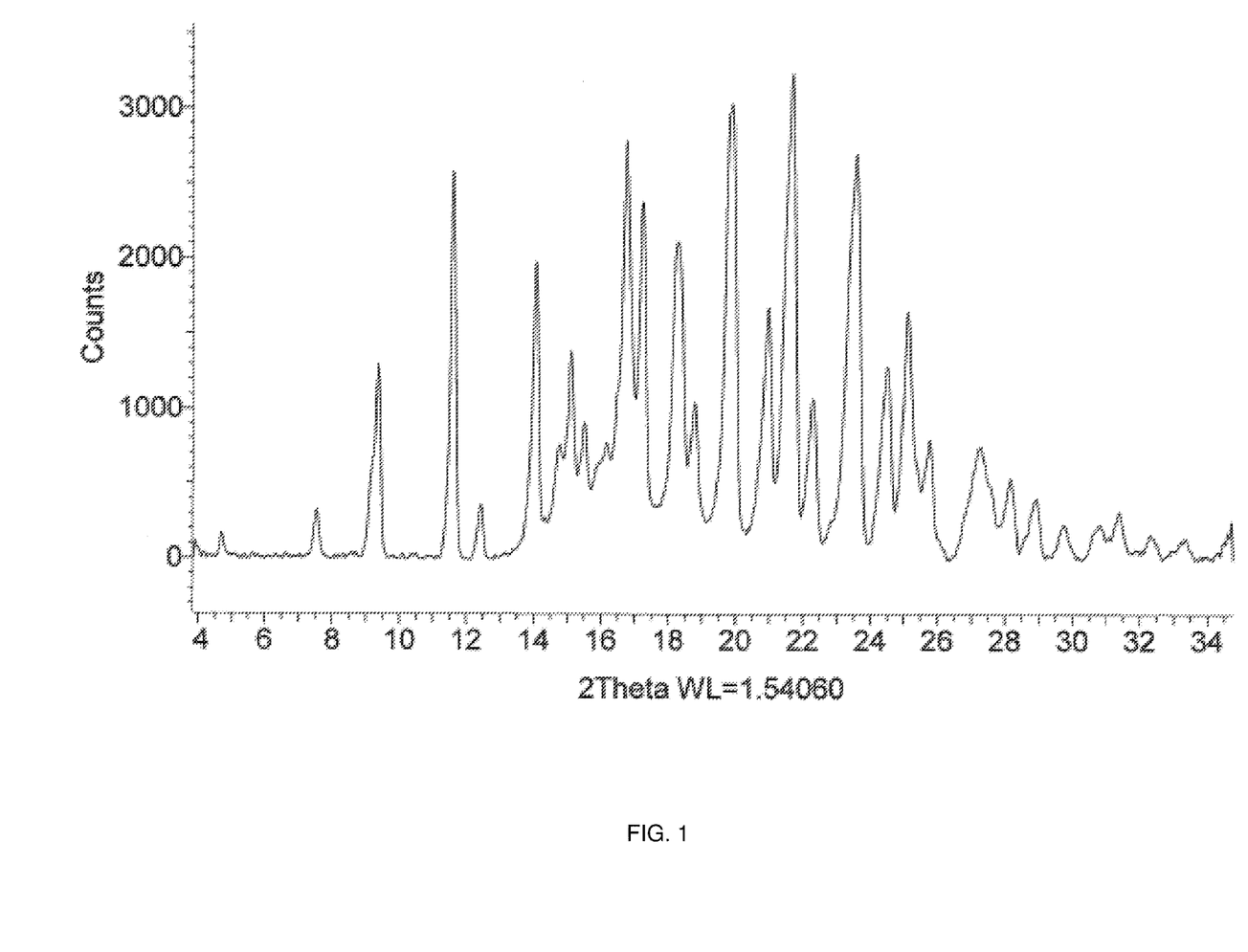
FIG. 1 is a representative PXRD diffractogram of Selexipag Form APO-I as prepared in Example 1.
Figure 3:
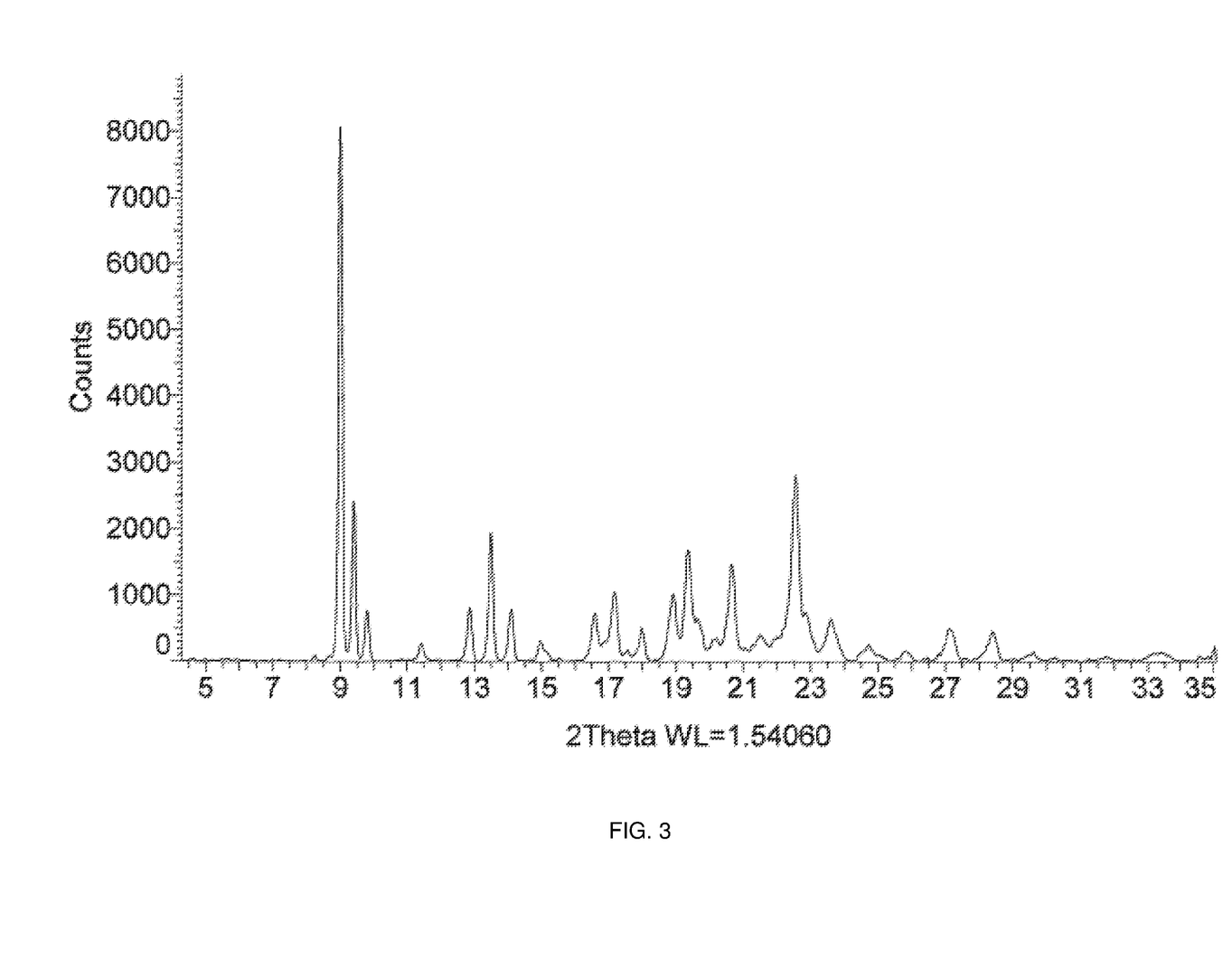
FIG. 3 is a representative PXRD diffractogram of seed crystals of Selexipag as prepared in Example 2.

Depending on the manner in which the embodiments of the invention are prepared, and the methodology and instrument used for PXRD analysis, the intensity of a given peak observed in the PXRD diffractogram may vary when compared to the same peak in the representative PXRD diffractograms provided in FIG. 1 and FIG. 3. Thus, differences in relative peak intensities between peaks in a PXRD diffractogram for a given crystalline form may be observed when compared to the relative peak intensities of the peaks in the representative PXRD diffractograms of FIG. 1 and FIG. 3. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIG. 1 and FIG. 3, it is understood that individual peak positions may vary between ±0.2° 2θ from the values observed in the representative PXRD diffractograms provided in FIG. 1 and FIG. 3 for the crystalline form of the invention, or listed in Table 1 and Table 2. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractograms provided in FIG. 1 and FIG. 3. Thus, PXRD diffractograms of the crystalline form of the present invention may, in some circumstances, display the same relative peak positions as observed in the representative PXRD diffractograms provided in FIG. 1 and FIG. 3, with the exception that each peak is offset in the same direction, and by approximately the same amount, such that the overall PXRD diffractogram is substantially the same in appearance as a PXRD diffractogram of FIG. 1 and FIG. 3, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIG. 1 and FIG. 3.

Figure 2:
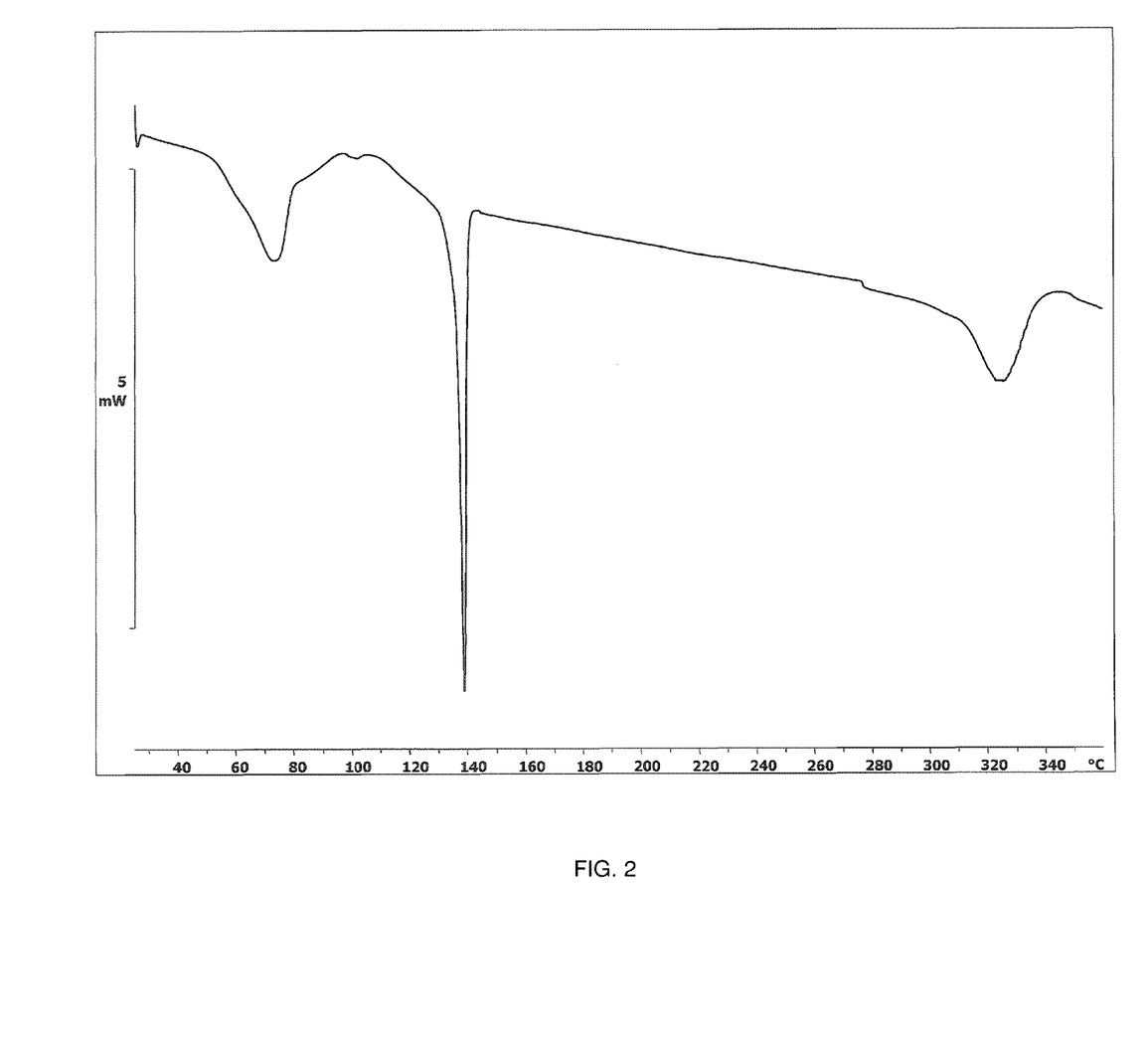
FIG. 2 is a representative DSC thermogram of Selexipag Form APO-I as prepared in Example 1.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermogram provided in FIG. 2 and described herein. Such variations are known and understood by a person of skill in the art, and any such variations do not depart from the invention disclosed herein.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of Selexipag. Single-component forms of Selexipag consist solely of Selexipag in the repeating unit of the crystal lattice. Multiple-component forms of Selexipag include solvates of Selexipag wherein a solvent is also incorporated into the crystal lattice.

Multi-component crystalline forms comprising more than one type of molecule, such as solvates, may have some variability in the exact molar ratio of their components depending on the conditions used for their preparation. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:0.5 should be understood to include the ratios 1:0.4 and 1:0.6, as well as all of the individual ratios in between.

As used herein, the term "room temperature" refers to a temperature in the range of 20° C. to 25° C.

Unless defined otherwise herein, the term "approximately", when used in reference to molar ratios, allows for a variance of plus or minus 10%. When reference is made to DSC thermograms, the use of approximately is intended to refer to a variance of ±2° C.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Selexipag, Selexipag Form APO-I, which is a methanol solvate of Selexipag. Preferably, in Selexipag Form APO-I, the molar ratio of Selexipag to methanol is approximately 1:0.5.

Selexipag Form APO-I can be characterized by a PXRD diffractogram comprising, among other peaks, characteristic peaks, expressed in degrees 2θ (±0.2°), at 7.5°, 12.4° and 21.7°. Preferably, the PXRD diffractogram further comprises at least three peaks, expressed in degrees 2θ (±0.2°), selected from the group consisting of 9.4°, 11.6°, 14.1°, 15.1°, 16.7°, 17.2°, 18.3°, 19.9°, 22.3° and 23.6°. More preferably, the PXRD diffractogram further comprises peaks, expressed in degrees 2θ (±0.2°), at 9.4°, 11.6°, 14.1°, 15.1°, 16.7°, 17.2°, 18.3°, 19.9°, 22.3° and 23.6°. PXRD studies of samples of Selexipag Form APO-I maintained under a nitrogen atmosphere in a sealed vial have shown that this crystal form is stable following storage at room temperature and ambient humidity for at least 14 days.

An illustrative PXRD diffractogram of Selexipag Form APO-I, as prepared in Example 1, is shown in FIG. 1. A peak listing, comprising representative peaks from the PXRD diffractogram in FIG. 1, and their relative intensities, is provided in Table 2. Although illustrative of the PXRD diffractogram that is provided for the Selexipag Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Selexipag Form APO-I from FIG. 1

| Angle (2θ) | Relative intensity (%) |
|---|---|
| 4.70 | 5.1 |
| 7.54 | 9.9 |
| 9.36 | 40.0 |
| 11.61 | 79.7 |
| 12.43 | 10.9 |
| 14.07 | 61.0 |
| 15.12 | 42.8 |
| 15.52 | 28.0 |
| 16.77 | 86.2 |
| 17.24 | 73.4 |
| 18.29 | 65.3 |
| 18.80 | 32.1 |
| 19.89 | 93.7 |
| 20.97 | 51.7 |
| 21.70 | 100.0 |
| 22.30 | 32.8 |
| 23.59 | 83.5 |
| 24.50 | 39.4 |

As described in Example 1, Selexipag Form APO-I can be prepared by dissolving Selexipag in methanol, preferably at elevated temperature, seeding the solution with the crystalline material obtained as in Example 2, followed by cooling, and maintaining the mixture at a suitable temperature, preferably to 0-5° C. Filtration of the resulting suspension, and drying in vacuo, preferably at room temperature, provides Selexipag Form APO-I having a PXRD diffractogram consistent with FIG. 1.

An illustrative DSC thermogram of Selexipag Form APO-I is shown in FIG. 2. The DSC thermogram may be further characterized by a first peak endotherm with an onset temperature of 55° C. and a peak maximum of 73° C. and by a second peak endotherm with an onset temperature of 136° C. and a peak maximum of 138° C.

Seed crystals for use in the preparation of Selexipag Form APO-I can, in the first instance, be prepared by the process described in Example 2. Surprisingly, the use of this seed material leads to the formation of Selexipag Form APO-I instead of the same crystalline form of the seeds themselves. Direct crystallizations of Selexipag from methanol in the absence of this seed material failed to produce Selexipag Form APO-I, consistent with a report in U.S. Pat. No. 8,791,122 B2 that recrystallization of Selexipag from methanol resulted in a mixture of Selexipag forms II and III. Following an initial preparation of Selexipag Form APO-I, seed crystals for future preparations are more conveniently reserved from this material, as described in Example 3.

An illustrative PXRD diffractogram of the crystalline Selexipag prepared in Example 2 is shown in FIG. 3. A peak listing, comprising representative peaks from the PXRD diffractogram in FIG. 3, and their relative intensities, is provided in Table 2. Although illustrative of the PXRD diffractogram that is provided for this novel Selexipag crystalline form, the relative intensities of the peaks are variable. Thus, depending on a particular sample, the prominence or relative intensity of the peaks observed may differ from those in the illustrative PXRD diffractogram and peak listing.

TABLE 2

Relative peak intensities of Selexipag seed crystals from FIG. 3

| Angle (° 2θ) | Relative intensity (%) |
| --- | --- |
| 9.01 | 100.0 |
| 9.41 | 29.7 |
| 9.81 | 9.4 |
| 11.42 | 3.4 |
| 12.86 | 10.0 |
| 13.49 | 23.9 |
| 14.10 | 9.7 |
| 14.97 | 3.8 |
| 16.59 | 9.1 |
| 17.17 | 12.9 |
| 17.99 | 6.3 |
| 18.92 | 12.6 |
| 19.35 | 21.2 |
| 20.66 | 18.7 |
| 22.55 | 35.1 |

In a further embodiment of the invention, there is provided a pharmaceutical composition comprising a methanol solvate of Selexipag with one or more pharmaceutically acceptable excipients. Preferably, the pharmaceutical composition is a solid dosage form suitable for oral administration, such as a capsule, tablet, pill, powder or granules. Most preferably, the pharmaceutical composition is a tablet. Preferably, the pharmaceutical composition provides a dose of Selexipag that is equivalent to the 0.2 mg, 0.4 mg, 0.6 mg, 0.8 mg, 1 mg, 1.2 mg, 1.4 mg or 1.6 mg of Selexipag found in UPTRAVI® tablets.

Suitable pharmaceutically acceptable excipients are preferably inert with respect to the methanol solvate of Selexipag, and may include, for example, one or more excipients selected from binders such as carboxymethyl cellulose sodium, methyl cellulose, hydroxypropyl methyl cellulose, gelatin, polyvinylpyrrolidone or polyvinyl alcohol; diluents or fillers such as starch or mannitol; lubricants and fluidizing agents such as colloidal silica, talc magnesium stearate, calcium stearate or polyethylene glycol; disintegrating or solubilizing agents such as carboxymethyl cellulose, carboxymethyl cellulose calcium, lowly-substituted hydroxypropyl cellulose, croscarmellose sodium, carboxymethyl starch sodium, calcium carbonate or sodium carbonate; a dissolution retarding agent such as paraffin; a resorbing agent such as a quaternary salt; or an absorbent such as bentonite or kaolin. Preferably, for the preparation of solid dosage forms, excipients are used in an appropriate fine size compatible to the fine size of the Selexipag to promote uniform mixing and dispersion within the dosage form. The preparation of solid oral dosage forms is well known to person of skill in the art, and is described generally, for example, in Remington The Science and Practice of Pharmacy 21$^{st}$ Edition (Lippincott Williams & Wilkins: Philadelphia; 2006; Chapter 45).

Optionally, the solid dosage forms may be prepared with coatings and shells, such as enteric coatings and extended release coatings, using standard pharmaceutical coatings. Such coatings, and their application, are well known to persons skilled in the art, and are described, for example, in Remington The Science and Practice of Pharmacy 21$^{st}$ Edition (Lippincott Williams & Wilkins: Philadelphia; 2006; Chapter 47).

EXAMPLES

The following non-limiting example is illustrative of some of the aspects and embodiments of the invention described herein.

The Selexipag used as a starting material in the following examples was consistent with Selexipag Form II, which is reported in U.S. Pat. No. 8,791,122 B2. However, other polymorphic forms are equally suitable as starting material, provided complete dissolution of the form occurs when preparing the novel crystalline form of Selexipag of the present invention.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54184 Å) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Differential Scanning Calorimetry Analysis:

DSC thermograms were collected on a Mettler-Toledo 821e instrument. Samples (1-5 mg) were weighed into a 40 μL aluminum pan and were crimped closed with an aluminum lid. The samples were analyzed under a flow of nitrogen (ca. 50 mL/min) at a scan rate of 10° C./minute.

Example 1: Preparation of Selexipag Form APO-I

Selexipag (200 mg, 0.40 mmol) and methanol (2.4 g) were mixed and the resulting suspension was heated to 66° C. for one hour to afford a yellow solution. The hot solution was filtered through a 0.45 μm syringe filter, seeded with material prepared as in Example 2 (ca. 2 mg) and immediately cooled to 0° C. by submersion in an ice-water bath. Precipitation was observed immediately and, after stirring for 4 hours at 0° C., the thick suspension was diluted with methanol (1.0 mL) and the solids were collected by filtration and dried in vacuo at room temperature overnight to afford Selexipag Form APO-I as a white solid (150 mg, 75% yield uncorrected for purity and solvent content). The PXRD diffractogram and DSC thermogram of a sample prepared by this method is shown in FIG. 1 and FIG. 2, respectively. $^1$H NMR analysis of the solid (d$_6$-DMSO, 300 MHz) indicated a molar ratio of Selexipag:methanol of approximately 1:0.5.

Material prepared by this method was used to seed further batches of Form APO-I demonstrating that the process of Example 2 is not integral to the ongoing production of Form APO-I following its initial preparation and the availability of Form APO-I seed crystals.

Example 2: Preparation of Seeds for Use in the Preparation of Selexipag Form APO-I Selexipag (50 mg, 0.10 mmol) and diethylene glycol (2.0 mL) were mixed and the resulting suspension was heated to 70° C. to afford a viscous yellow solution. The solution was allowed to cool to room temperature and then placed in a refrigerator (2-8° C.). Precipitation was observed after 10 days, and the solids were collected by filtration, washed with MTBE (2.0 mL) and dried on the funnel to give a white solid. The PXRD diffractogram of a sample prepared by this method is shown in FIG. 3. This solid was used as seed crystals in Example 1.

Example 3: Preparation of Selexipag Form APO-I

Selexipag (1.0 g, 2.0 mmol) and methanol (4.4 g) were mixed and the resulting suspension was heated to 70° C. for two hours to afford a yellow solution. The hot solution was filtered through a 0.45 μm syringe filter, seeded with material prepared as in Example 1 (ca. 2 mg) and immediately cooled to 0° C. by submersion in an ice-water bath. Precipitation was observed immediately and, after stirring for 2 hours at 0° C., the thick suspension was diluted with methanol (1.0 mL) and the solids were collected by filtration and dried in vacuo at room temperature overnight to afford Selexipag Form APO-I as a white solid (850 mg, 85% yield uncorrected for purity and solvent content) having a PXRD diffractogram consistent with FIG. 1.

What is claimed is:

1. A methanol solvate of Selexipag, Form APO-I, characterized by a PXRD diffractogram comprising peaks, expressed in degrees 2θ (±0.2°), at 7.5°, 12.4° and 21.7°.

2. The methanol solvate of claim 1, wherein the molar ratio of Selexipag to methanol is between approximately 1:0.25 and approximately 1:0.75.

3. The methanol solvate of claim 2, wherein the molar ratio of Selexipag to methanol is approximately 1:0.5.

4. The methanol solvate of claim 1, further comprising at least three peaks, expressed in degrees 2θ (±0.2°), selected from the group consisting of: 9.4°, 11.6°, 14.1°, 15.1°, 16.7°, 17.2°, 18.3°, 19.9°, 22.3° and 23.6°.

5. The methanol solvate of claim 1, further comprising peaks, expressed in degrees 2θ (±0.2°), at 9.4°, 11.6°, 14.1°, 15.1°, 16.7°, 17.2°, 18.3°, 19.9°, 22.3° and 23.6°.

6. The methanol solvate of claim 1, characterized by a DSC thermogram comprising an endothermic peak with a peak onset of 55° C. and a peak maximum of 73° C.

7. The methanol solvate of claim 4, characterized by a DSC thermogram comprising an endothermic peak with a peak onset of 55° C. and a peak maximum of 73° C.

8. The methanol solvate of claim 4, wherein the molar ratio of Selexipag to methanol is approximately 1:0.5.

9. The methanol solvate of claim 1, providing a PXRD diffractogram comprising peaks in substantially the same positions (±0.2° 2θ) as those shown in FIG. 1.

10. A process for the preparation of a methanol solvate of Selexipag, Form APO-I, characterized by a PXRD diffractogram comprising peaks, expressed in degrees 2θ (±) 0.2°, at 7.5°, 12.4° and 21.7°, the process comprising:

(1) dissolving Selexipag in methanol at a suitable temperature to provide a solution;
(2) seeding the solution with:
 (a) first seeds comprising a methanol solvate of Selexipag characterized by a PXRD diffractogram comprising peaks, expressed in degrees 2θ (±0.2°), at 7.5°, 12.4° and 21.7°;
 (b) second seeds comprising a crystalline form of Selexipag providing a PXRD diffractogram comprising peaks, expressed in degrees 2θ (±0.2°), at 9.8°, 12.9° and 13.5°, obtained following crystallization of Selexipag from diethylene glycol; or
 (c) a combination of the first and second seeds;
to provide a mixture;
(3) cooling the mixture, if necessary, to form a suspension; and
(4) filtering the suspension to isolate the methanol solvate of Selexipag.

11. The process of claim 10, wherein the solution is seeded with the first seeds.

12. The process of claim 10, wherein the solution is seeded with the second seeds.

13. The process of claim 10, wherein the suitable temperature is between approximately 50° C. and approximately 70° C.

14. The process of claim 10, wherein the mixture is cooled to a temperature of between approximately 0° C. and approximately 5° C.

15. The process of claim 10, wherein the molar ratio of Selexipag to methanol in the methanol solvate is between approximately 1:0.25 and approximately 1:0.75.

16. The process of claim 15, wherein the molar ratio of Selexipag to methanol in the methanol solvate is approximately 1:0.5.

17. A pharmaceutical composition comprising the methanol solvate of claim 1, and one or more pharmaceutically acceptable excipients.

18. The pharmaceutical composition of claim 17, wherein the pharmaceutical composition is a tablet.

19. The pharmaceutical composition of claim 18, wherein the pharmaceutical composition comprises an amount of the methanol solvate equivalent to 0.2 mg, 0.4 mg, 0.6 mg, 0.8 mg, 1 mg, 1.2 mg, 1.4 mg or 1.6 mg Selexipag.

* * * * *

UNITED STATES PATENT AND TRADEMARK OFFICE
CERTIFICATE OF CORRECTION

PATENT NO. : 10,407,396 B2
APPLICATION NO. : 16/185223
DATED : September 10, 2019
INVENTOR(S) : Fabio E. S. Souza et al.

Page 1 of 1

It is certified that error appears in the above-identified patent and that said Letters Patent is hereby corrected as shown below:

Column 11, Line 45, Claim 10, delete "(±) 0.2°," and insert -- (±0.2°), --

Signed and Sealed this
Twenty-sixth Day of November, 2019

Andrei Iancu
*Director of the United States Patent and Trademark Office*